United States Patent [19]

Meinert et al.

[11] Patent Number: 5,260,496
[45] Date of Patent: Nov. 9, 1993

[54] PROCESS FOR SEPARATING MIXTURES OF PREFLUORINATED HYDROCARBON COMPOUNDS

[75] Inventors: Hasso Meinert; Juergen Mader, both of Ulm, Fed. Rep. of Germany

[73] Assignee: Kali-Chemie AG, Hanover, Fed. Rep. of Germany

[21] Appl. No.: 835,462

[22] PCT Filed: Aug. 28, 1990

[86] PCT No.: PCT/DE90/00658
§ 371 Date: Feb. 28, 1992
§ 102(e) Date: Feb. 28, 1992

[87] PCT Pub. No.: WO91/03442
PCT Pub. Date: Mar. 21, 1991

[30] Foreign Application Priority Data

Aug. 30, 1989 [DE] Fed. Rep. of Germany ....... 3928692

[51] Int. Cl.$^5$ ............................................. C07C 17/38
[52] U.S. Cl. .................................................. 570/179
[58] Field of Search ......................................... 570/179

[56] References Cited

U.S. PATENT DOCUMENTS 3,215,747 11/1965 Fairberg et al. ................... 570/179
4,906,796 3/1990 Yates .................................. 570/179

OTHER PUBLICATIONS

Hersh "Molecular Sieves" (1961). pp. V, VII, 1-4, 78-81 Reinhold Pub. Co., Chapman & Hill Ltd. London.

Primary Examiner—Marianne M. Cintins
Assistant Examiner—John Peabody
Attorney, Agent, or Firm—Evenson, McKeown, Edwards & Lenahan

[57] ABSTRACT

A process for separation of mixtures of partially- or perfluorinated hydrocarbon compounds, which optionally contain additional chain members from the heteroatom group nitrogen, oxygen, boron, phosphorus and sulfur and/or can be substituted by further halogen atoms, characterized in that such partially- or perfluorinated compounds, which have an acyclic straight-chain structure and a critical molecule diameter in the range from 4 to 7 Å or are substituted by residues with a straight-chain acyclic structure and with a critical molecule diameter in the range from 4 to 7 Å, of such partially- or perfluorinated compounds, which have no straight-chain acyclic residues, and whose critical molecule diameter amounts to at least 1.1-fold times the that of the aforementioned straight-chain acyclic residues, in liquid or gaseous phase are separated in that a mixture or a solution of the mixture in an inert organic solvent, the molecular diameter of which is larger that of the aforementioned straight-chain acyclic residue, is contacted with an amount of a molecular sieve sufficient for adsorption, the average pore diameter of which lies in the range of the critical molecule diameter of the aforesaid acyclic residue or up to 30% less, separating the molecular sieve laden predominantly with compounds containing acyclic residues, and desorbing the compounds adsorbed on the molecular sieve.

18 Claims, No Drawings

PROCESS FOR SEPARATING MIXTURES OF PREFLUORINATED HYDROCARBON COMPOUNDS

The present invention relates to a process for separating mixtures of perfluorinated or partially perfluorinated hydrocarbon compounds, especially perfluorocarbon mixtures as obtained in the electrochemical perfluorination of cyclic hydrocarbons.

The so-called "Perfluorkohlenstoffe" (=perfluorocarbons) are perfluorinated organic compounds which consist of carbon and fluorine and may also contain hetero atoms such as nitrogen or oxygen, for example. Perfluorocarbons are chemically and biologically inert compounds insoluble in water, which can have a fluid to waxy consistency at room temperature under standard pressure. Such compounds are disclosed, for example, in European patent applications, publication numbers 77 114, 99 652 and 151 679. The perfluorocarbon molecules are outstandingly masked by a uniform shell of fluorine atoms. Therefore perfluorocarbons are extraordinarily inert chemically and physiologically, i.e., nontoxic. On account of their extremely low intermolecular forces perfluorocarbons have a low boiling point in comparison to their molecular masses and an extremely low surface tension. The very weak intermolecular forces also result in the ability of the perfluorocarbons to dissolve large amounts of gases, such as oxygen or carbon dioxide, for example. On the basis of these properties, especially their ability to dissolve and transport oxygen physically, perfluorocarbons have found application in medicine for the preparation of aqueous oxygen-transporting perfluorocarbon emulsions which can be used, for example, as blood substitutes or perfusion media. Furthermore, perfluorocarbons are also appropriate for use in other technical fields in which nontoxic and chemically inert liquid or waxy substances are needed, or inert substances with the ability to dissolve gases are needed. Thus, perfluorocarbons and their mixtures are suitable as inert refrigerants, lubricants, sealing and hydraulic fluids, insulating media in electrical technology, and means for vapor-phase soldering or as additives in agents for the above-mentioned purposes.

Perfluorinated or partially fluorinated hydrocarbon compounds are generally obtained in a manner known in itself by fluorination, e.g., electrochemical fluorination of corresponding nonfluorinated hydrocarbon compounds. In the fluorination of cyclic starting compounds, mixtures are often obtained which contain, in addition to the partially or perfluorinated cyclic products, likewise partially fluorinated byproducts or perfluorinated and hence chemically and physiologically inert byproducts, which have acyclic structural elements. In particular, fluorination products of cyclic starting compounds can contain such perfluorinated byproducts which have a molecular weight similar to that of the chief product, and thus boil in the same temperature range as the chief product, as for example isomers of the chief product containing acyclic structural elements. Such mixtures cannot be separated satisfactorily by fractional distillation. For many applications the mixtures can be used as-is because the presence of perfluorinated byproducts does not cause the application to be impaired. In other fields of application, however, in medicine for example, pure compounds are required.

It is the object of the present invention to find a simple separating process which can be used for separating mixtures of perfluorinated or partially fluorinated hydrocarbon compounds which contain cyclic compounds and compounds having acyclic structural elements.

The subject matter of the present invention is a process for the separation of mixtures of partially or perfluorinated hydrocarbon compounds which may still contain chain links from the group of the hetero atoms, nitrogen, oxygen, boron, phosphorus and sulfur, and/or can be substituted by additional halogen atoms, characterized in that such partially or perfluorinated compounds which have an acyclic straight-chain structure and a critical molecule diameter ranging from 4 to 7 Å, or are substituted by moieties having a straight-chain acyclic structure and a critical molecule diameter ranging from 4 to 7 Å, and which are hereinafter called A compounds, are separated in liquid or gaseous phase from those partially or perfluorinated compounds which have no straight-chain acyclic moieties and whose critical molecule diameter amounts at least to 1.1 times that of the aforesaid straight-chain acyclic moieties, and which are substituted only by those moieties whose critical molecule diameter amounts to at least 1.1 times that of the aforesaid straight-chain acyclic moieties, and which hereinafter are called B compounds, by:

a) the mixture or a solution of the mixture in an inert organic solvent whose molecular diameter is greater than that of the aforesaid straight-chain acyclic moiety is placed in contact with a quantity of a molecular sieve sufficient for the adsorption of the A compounds, the average pore opening diameter of the molecular sieve being in the range of the critical molecule diameter of the acyclic straight-chain moiety of the A compounds or up to 30% below it, b) the molecular sieve laden chiefly with A compounds is separated from the liquid or gaseous phase depleted of A compounds and containing the B compounds, and c) the compounds adsorbed on the molecular sieve are desorbed.

The process of the invention is especially suited for the separation of mixtures of perfluorocarbons containing in some cases hetero atoms from the group, nitrogen and oxygen, and containing, as B compounds, perfluorocarbons with a cyclic structure containing hetero atoms in some cases and, as A compounds, perfluorocarbons with an acyclic structure containing hetero atoms in some cases or contain moieties with an acyclic structure. In the scope of the present invention, saturated or aromatic, especially saturated, perfluorinated organic compounds which consist of carbon and fluorine and can in some cases also contain hetero atoms such as nitrogen, oxygen or sulfur, especially nitrogen or oxygen, in the carbon chain are called perfluorocarbons. The compounds can contain, for example, up to 20, especially 5–20 carbon atoms. Perfluorocarbons of the B compound type are, for example, mono- to tetracyclic compounds with 3–18, especially 6–12 ring members. They can be compounds with annulated ring systems, such as decalin [decahydronaphthalene] for example, or with diamantoid ring systems, such as adamantane for example, or compounds wherein two 5-member and/or 6-member rings are joined together, in some cases by a lower alkylene chain, such as cyclohexylmorpholine or 1,3-dipiperidinopropane. The process is likewise also suited for the separation of mixtures of fluorinated A and B compounds which still contain a residue of hydrogen atoms, i.e., are only partially fluorinated, or which are substituted by additional halogen atoms. The process is suited especially for separating mixtures which contain a cyclic B compound and were obtained by fluorination, especially electrochemical fluorination of the nonfluorinated starting compound corresponding to the cyclic B compound. For example, the process is suitable for separating mixtures which contain cyclic B compounds, especially perfluorocarbons with a cyclic structure, containing hetero atoms in some cases, also isomeric A compounds which have an acyclic structure or contain moieties with an acyclic structure. The process is also suitable for separating mixtures which contain compounds of formula B, especially cyclic perfluorocarbons with a cyclic structure containing hetero atoms in some cases, along with homologous A compounds substituted by lower straight-chain perfluoroalkyl moieties, especially trifluoromethyl moieties.

The critical molecule diameter of compounds can be calculated, for example by using the van der Waals atomic radii (cf. O. Grubner et al., "Molekularsiebe," VEB Deutscher Verlag der Wissenschaften, Berlin 1968, pages 63-64). The critical diameter of spherical molecules (e.g., noble gases) is equal to the diameter of a sphere describing this molecule.

In the case of symmetrical molecules disposed tetrahedrically (e.g., $CCl_4$), the critical diameter is equal to the diameter of the circle which describes the triangular wall of the tetrahedron.

In the case of molecules arrayed octahedrically (e.g., $SF_6$) the critical diameter is equal to the diameter of the circle that gives the square base of the octahedron. In the case of diatomic molecules their critical diameter is given by the diameter of the circle that describes these molecules in the plane perpendicular to their length. The critical diameters of n-paraffins whose molecules have a linear (zig-zag) arrangement are given by the diameter of the largest circle that describes the molecules lying in the plane perpendicular to the paraffin chain, and they are the same in all n-paraffins. Similar considerations apply also to acyclic perfluorocarbon compounds and moieties.

Suitable as molecular sieve for the process of the invention are especially inorganic molecular sieves, such as aluminosilicates or silicalites. Natural and synthetic zeolites, especially type A and X zeolites, have proven effective. The pore size of the molecular sieves used can vary according to the critical molecule diameter of the straight-chain, acyclic moieties of the A compounds. In general, good separating effects are obtained with molecular sieves with mean pore opening diameters of 4.5 to 6.5 Ångstroms. The molecular sieves can be used as particles of varying shape, e.g., in the form of granules or pearls.

Mixtures of cyclic perfluorocarbons containing hetero atoms in some cases with acyclic perfluorinated byproducts containing straight-chain moieties, which can be separated by the process of the invention, can be obtained, for example, by fluorinating corresponding nonfluorinated cyclic compounds by methods known in themselves. The nonfluorinated starting compounds can be fluorinated by electrochemical fluorination by electrolyzing solutions of the compounds in liquid hydrofluoric acid. It is expedient to use for this purpose solutions of 4-30, preferably 5-10 wt.-% of an unfluorinated starting compound in liquid hydrofluoric acid. The electrolysis is advantageously performed at temperatures between $-25°$ and $+10°$ C., preferably $-5°$ and $+5°$ C., an anode current density of 2-30 mA/cm$^2$, and a cell voltage of 3-10, especially 4-8 volts. For further processing, the raw reaction product settling as a heavy phase on the bottom of the electrolysis cell is separated and, to decompose any partially fluorinated byproducts, it is subjected to a treatment with an alkali metal or alkaline earth metal base, especially an alkali metal or alkaline earth metal hydroxide, in the presence of water and, if desired, a lower aliphatic primary or secondary amine at a temperature sufficiently high to decompose any partially fluorinated byproducts. This step of the process can be performed by methods known in themselves. For example, the reaction mixture can be heated for a period of several hours to 8 days at ebullition with refluxing. The perfluorinated compounds can be isolated from the reaction mixture by fractional distillation. The products separated from the reaction mixture by fractional distillation are generally free of unperfluorinated products. In general, however, they are mixtures which contain, in addition to the perfluorinated cyclic chief product, perfluorinated byproducts which are isomeric to the chief product or have a molecular weight similar to that of the chief product and may contain acyclic moieties. For example, in compounds containing piperidine rings, a narrowing of the ring sometimes occurs under the conditions of the electrochemical perfluorination, so that to a lesser extent isomeric methylpyrrolidine compounds form in addition to the perfluorinated piperidine compounds. Such isomer mixtures can for example be separated by the process of the invention.

According to the invention, the contacting of the mixture to be separated with the molecular sieve can be performed in a liquid phase or in a gas phase. The adsorption is the liquid phase can be performed at temperatures between room temperature and the boiling temperature of the mixture being separated. For example, mixtures of compounds liquid at room temperature or solutions of mixtures of compounds that are waxy to solid at room temperature can be introduced into a reactor containing the molecular sieve and kept therein in contact with the molecular sieve for a period of time sufficient for the adsorption of the A compounds containing straight-chain acyclic moieties. Suitable solvents are especially liquid perfluorocarbons, such as perfluorinated decalin. Provision is made for a thorough mixing of the mixture with the molecular sieve particles by shaking or stirring, for example. The adsorption of A compounds onto the molecular sieve can be performed at room temperature or at elevated temperatures below the boiling point of the reaction mixture. The amount of molecular sieve to be used can vary according to the type of molecular sieve and the type of adsorbing A compound. For example, 2-50 times the weight of the A compound to be adsorbed can be used. The contact of the molecular sieve with the mixture to be separated can also be performed in the gas phase by passing the mixture in gas form through a reactor filled with molecular sieve particles. For example, the mixture can be passed by means of an evaporator together with a carrier gas through the reactor containing the molecular sieve with such a velocity of flow that the time of contact with the molecular sieve suffices for the adsorption of the formula A compound. The adsorption from the gas phase can be performed at temperatures between 50° and 300° C. and at pressures from 0.1 to 10 bar.

After the adsorption of the A compounds is performed, the molecular sieve laden with compound A is separated from the unadsorbed compounds B. After a gas phase adsorption this can be performed by flushing out with carrier gas. If the adsorption was performed from the liquid phase, the molecular sieve particles laden with compounds A can be separated in a manner known in itself by filtering or decanting the unadsorbed liquid. The molecular sieve particles can also be laden with small amounts of molecules of compound B adhering externally, for example, depending on the amount and volume of the adsorbed molecules of compound A.

The subsequent desorption of the formula A compounds from the molecular sieve particles can be performed in a manner known in itself, for example by displacement desorption or by driving them out with heat. A displacement desorption can be performed in a manner known in itself, for example, by treating the molecular sieve laden with compounds A with water. If the molecular sieve particles still contain small amounts of B compounds, a thermal desorption is recommended. In this case, B compounds adhering externally can first be evaporated and then the adsorbed A compounds can be desorbed by further heating. The thermal desorption can be performed by raising the temperature to a range between ebullition and the degradation temperature of the compounds to be desorbed. The desorption temperature can best be about 100° to 150° C. above the adsorption temperature in the gas phase. If the mixture being separated contains several adsorbable A compounds, a mixture of these A compounds can also be obtained by the desorption. Such mixtures of A compounds can be further separated, if desired, by chromatography in a manner known in itself, e.g., by thin-layer or gas chromatography.

In accordance with the process of the invention, molecular sieves are used whose pore opening diameters are up to 30% below the critical molecule diameter of the A compounds to be adsorbed. Since the pore opening diameters of the molecular sieves used are thus smaller than the critical molecule diameter of all compounds contained in the mixture being separated, it is surprising that nevertheless a separation of the A compounds from the B compounds is possible by adsorption onto molecular sieves, such as zeolites, by the process of the invention.

The following examples are intended to further explain the invention without, however, limiting its scope.

EXAMPLE 1

Separation of a mixture of perfluorodecalin and perfluoromethyldecalin 10 g of a zeolitic molecular sieve with a mean pore opening diameter of 0.5 nm (Mfr. Merck) was activated by 15 hours of heat treatment at 500° C. in the muffle kiln. 4 g of perfluorodecalin and 4 g of perfluoromethyldecalin were added to the molecular sieve particles thus treated, in a glass flask and shaken for two hours at room temperature. Then the unadsorbed liquid was separated from the molecular sieve. The unadsorbed phase contained about 4 g of pure perfluorodecalin. For the desorption of the adsorbed compound the molecular sieve particles in the glass flask were shaken with water for two hours at room temperature. The desorbed product was separated from the water by distillation into a chilled receiver and identified by gas chromatography and by $^{19}F$ NMR spectroscopy as perfluoromethyldecalin. The yield of perfluoromethyldecalin was about 3.5 g.

EXAMPLE 2

Separation of a mixture of perfluorotrimethyl adamantane and perfluoroadamantane 0.5 g of perfluorotrimethyl adamantane and 0.5 g of perfluoroadamantane were dissolved in 15 g of perfluorodecalin. The solution was shaken with 20 g of the activated molecular sieve used in Example 1 (pore opening diameter 0.5 nm) for four hours at a temperature of 30°–40° C. Then the unadsorbed liquid was separated from the molecular sieve particles. The liquid contained the weighed-in amount of perfluoroadamantane and perfluorodecalin. The desorption of the adsorbed part of the starting mixture was performed by heating the molecular sieve at 180° C. at reduced pressure (oil-pump vacuum) and collecting the volatilized product in a chilled receiver. Approximately 0.3 g of perfluorotrimethyl adamantane was obtained, which was identified by $^{19}F$-NMR spectroscopy and mass spectrometry.

EXAMPLE 3

Separation of a mixture of perfluorocyclohexyl morpholine and perfluoro-n-hexylmorpholine A) Preparation of the mixture:

A 5 to 15 percent solution of morpholinocyclohexene-(1) in predried, chilled, liquid hydrofluoric acid was perfluorinated in an electrolysis cell at an anode current density of 3–10 mA/cm$^2$, a cell voltage of 5 to 6.5 V and a cell temperature of $-8°$ to $+5°$ C. From time to time additional morpholinocyclohexene-(1) was added and consumed hydrofluoric acid was replaced so as to permit continuous operation of the cell. The heavy phase gathering on the cell floor and containing the crude reaction product was let out from time to time. The crude product was treated with the same volumes each time of an aqueous 8N potassium hydroxide solution and dibutylamine. The mixture was refluxed for 8 days. Then the mixture was fractionally distilled. In the distillation a chief fraction is obtained boiling in the range of 145°–148° C. The gas chromatographic analysis showed that the distillate was a mixture of 65% perfluorocyclohexyl morpholine, 33% perfluoro-n-hexyl-morpholine and 2% other byproducts.

B) Separation of the mixture obtained under A):

The above-obtained mixture of perfluorocyclohexyl morpholine and perfluoro-n-hexyl morpholine at 120° C. was fed through an evaporator into a glass column filled with a zeolitic molecular sieve with a pore size of 5 Ångstroms, through which a constant stream of helium was flowing at a rate of 60 ml/minute. While the perfluorocyclohexyl morpholine was passing through the column, the byproduct containing the $C_6F_{13}$ moiety was held back. Thus, perfluorinated cyclohexyl morpholine was obtained with a boiling point of 147.5° to 149.5° C. After all of the perfluorocyclohexyl morpholine and excess perfluoro-n-hexylmorpholine had left the column the temperature was raised to 300° C. In a cold trap at the outlet of the column, pure perfluoro-n-hexyl morpholine condensed, which had a boiling point of 149° to 150° C.

EXAMPLE 4

Separation of a mixture of perfluorinated 1,3-dipiperidinopropane and the perfluorinated 1-(3-methylpyrrolidino)-3-piperidinopropane isomeric therewith, and 1,3-di(3-methylpyrrolidino)-propane.

A) Preparation of the mixture:

A 10% solution of 1,3-dipiperidinopropane in pre-dried, chilled liquid hydrofluoric acid was perfluorinated in an electrolysis cell at a temperature of +2° C., an anode current density of 2.5 to 25 m/cm$^2$ and a cell voltage of 4.5 to 7.0 V. From time to time dipiperi-dinopropane dissolved in liquid hydrofluoric acid was added and consumed hydrofluoric acid was replaced so as to permit the cell to operate continuously. The raw reaction product collecting on the cell bottom was let out from time to time and processed as described in Example 3A. In the distillation a chief fraction was obtained which boiled at 195° to 203° C. A gas chromatographic separation of the mixture showed that it contained 58% of perfluorinated 1,3-dipiperidinopropane, 36% of perfluorinated 1-(3-methylpyrroli-dino)-3-piperidinopropane, and 6% of perfluorinated 1,3-di(3-methylpyrrolidino)-propane.

B) Separation of the mixture obtained above:

The separation was performed by means of temperature-programmed gas chromatography on a preparative gas chromatograph. The mixture was passed through a gas chromatography separating column filled with a zeolite molecular sieve with a pore size of 5 Å (glass column 1.7 mm × 3 mm inside diameter) at about 180° C. While the perfluorinated 1,3-dipiperidinopropane was passing through the column, the two byproducts containing a trifluoromethyl moiety were largely held back. Thus a pure perfluorinated 1,3-dipiperidinopropane was obtained with a boiling point of 191° C. After all of the perfluorinated 1,3-dipiperidinopropane had left the column, thermal desorption at a temperature raised by 100° C. yielded a mixture of perfluorinated 1-(3-methylpyrrolidino)-3-piperidinopropane and perfluorinated 1,3-di-(3-methylpyrrolidino)-propane was obtained. Then the separation of the two compounds containing trifluoromethyl moieties was performed by preparative gas chromatography on a solid phase of methylsilicone oil on inorganic support material (=SE-30, Mfr. Chrompack). Perfluorinated 1-(3-methylpyrrolidino)-3-piperidinopropane with a boiling point of 189° C. and 1,3-di(3-methylpyrrolidino)-propane with a boiling point of 186° C. was obtained.

We claim:

1. A method of separating a mixture comprising:
   A) at least one cyclic perfluorinated compound substituted by an unbranched acyclic residue, said acyclic residue having a critical molecule diameter ranging from 4 to 7 Å, and
   B) at least one cyclic perfluorinated compound which has no unbranched acyclic moieties and whose critical molecule diameter is at least 1.1 times that of said unbranched acyclic residue, said cyclic perfluorinated compound having no unbranched acyclic moieties being substituted only by moieties having critical molecule diameters amounting to at least 1.1 times that of said unbranched acyclic residue, said process comprising the steps of:
   a) contacting said mixture with a quantity of a molecular sieve sufficient to adsorb the cyclic perfluorinated compound substituted by an unbranched acyclic residue, said molecular sieve having an average pore opening diameter in the range from the critical molecule diameter of said unbranched acyclic residue to 30% less than the critical molecule diameter of said unbranched acyclic residue,
   b) separating the molecular sieve laden with adsorbed cyclic perfluorocarbon compound substituted by an unbranched acyclic residue from a residual mixture depleted in cyclic perfluorocarbon compound substituted by an unbranched acyclic residue and containing the cyclic perfluorocarbon compound which has no unbranched acyclic moieties, and
   c) desorbing the adsorbed cyclic perfluorocarbon compound substituted by an unbranched acyclic residue from the molecular sieve.

2. A process according to claim 1 wherein compounds of said mixture contain hetero atom chain members selected from the group consisting of nitrogen, oxygen, boron, phosphorus and sulfur.

3. A process according to claim 1, wherein compounds of said mixture are substituted by additional halogen atoms.

4. A process according to claim 1, wherein said contacting step is effected by contacting said molecular sieve with a solution of said mixture in an inert organic solvent.

5. A process according to claim 1, wherein said contacting step is carried out in liquid phase.

6. A process according to claim 1, wherein said contacting step is carried out in gaseous phase.

7. A method according to claim 1, wherein said mixture to be separated is a mixture of A') cyclic perfluorocarbon compounds containing hetero atoms and substituted with unbranched acyclic residues, and B') cyclic perfluorocarbon compounds containing hetero atoms selected from the group consisting of nitrogen and oxygen and free of unbranched acyclic substituents.

8. A method according to claim 1, wherein said mixture to be separated is a product mixture from fluorination of an un-fluorinated cyclic compound corresponding to said perfluorinated compound which has no unbranched acyclic moieties.

9. A method according to claim 8, wherein said fluorination is electrochemical fluorination.

10. A method according to claim 1, wherein said mixture to be separated is an isomer mixture comprising a cyclic perfluorocarbon compound which has no unbranched acyclic moieties and a cyclic perfluorocarbon compound which carries an unbranched acyclic residue, said compound which carries an unbranched acyclic residue being an isomer of said compound which has no unbranched acyclic moieties.

11. A method according to claim 1, wherein said mixture to be separated is an homolog mixture comprising a cyclic perfluorocarbon compound which has no unbranched acyclic moieties and a corresponding cyclic perfluorocarbon compound substituted by an unbranched acyclic perfluoroalkyl moiety.

12. A method according to claim 11, wherein said unbranched acyclic perfluoroalkyl moiety is a trifluoromethyl group.

13. A method according to claim 1, wherein said molecular sieve is an inorganic molecular sieve.

14. A method according to claim 1, wherein said molecular sieve is selected from the group consisting of natural and synthetic zeolites.

15. A method according to claim 1, wherein said molecular sieve has a mean pore opening diameter of from 5 to 6.5 Å.

16. A method according to claim 1, wherein said cyclic perfluorocarbon compound substituted by an unbranched acyclic residue has a molecular diameter greater than the critical molecule diameter of said unbranched acyclic residue.

17. A method according to claim 1, wherein said unbranched acyclic residue is partially fluorinated.

18. A method according to claim 1, wherein said unbranched acyclic residue is perfluorinated.

* * * * *